United States Patent [19]

Pesa et al.

[11] 4,390,639

[45] Jun. 28, 1983

[54] UPGRADING SYNTHESIS GAS

[75] Inventors: Frederick A. Pesa, Aurora; Anne M. Graham, Northfield, both of Ohio

[73] Assignee: The Standard Oil Company, Cleveland, Ohio

[21] Appl. No.: 332,773

[22] Filed: Dec. 21, 1981

[51] Int. Cl.$^3$ ............... C07C 1/04; C07C 7/163; C07C 29/15

[52] U.S. Cl. ............... 518/713; 518/726; 252/474; 252/466 PT; 252/460; 252/455 R

[58] Field of Search ............... 518/713, 726

[56] References Cited

U.S. PATENT DOCUMENTS 2,535,060 12/1950 Gresham .
2,549,470 4/1951 Howk et al. .
4,086,262 4/1978 Chang et al. .
4,171,320 10/1979 Vannice et al. .
4,199,522 4/1980 Marchison et al. .
4,206,134 6/1980 Kugler et al. .
4,215,019 7/1980 Drake et al. .
4,246,186 1/1981 Bhosin .

OTHER PUBLICATIONS

Galvagno et al., J. of Cat., 69, 283-291, 1981.

Primary Examiner—Howard T. Mars
Attorney, Agent, or Firm—Joseph G. Curatolo; Herbert D. Knudsen; Larry W. Evans

[57] ABSTRACT

A process for the upgrading of synthesis gas is provided wherein olefin and oxygenated hydrocarbons, particularly alcohol and carboxylic acid, products predominate. The process includes contacting synthesis gas at elevated temperature and pressure in the presence of a catalyst comprising partially reduced ruthenium oxide and elemental gold. The products may be recovered and contacted with hydrogen at elevated temperature and pressure in the presence of a hydrogenation catalyst to yield alkanes, alcohols and esters useful for fuels.

16 Claims, No Drawings

UPGRADING SYNTHESIS GAS

TECHNICAL FIELD

The present invention is directed to the upgrading of synthesis gas to produce mixtures of hydrocarbons.

More particularly, the present invention is directed to a vapor phase reaction of synthesis gas comprising carbon monoxide and hydrogen in the presence of a catalyst to produce mixtures of hydrocarbon and oxygenated hydrocarbons, wherein olefin, alcohol and carboxylic acid products predominate.

BACKGROUND OF THE INVENTION

U.S. Pat. Nos. 2,535,060 to Gresham and 2,549,470 to Howk et al. disclose the preparation of straight-chain primary hydroxyalkanes by introducing hydrogen, carbon monoxide and a hydroxylated solvent into a reaction vessel and heating the mixture in the presence of a ruthenium-containing catalyst (particularly ruthenium metal, oxide, carbonyl, or salts of carboxylic acids which give rise to formation of the carbonyl) and in Howk et al., in the presence of an alkaline reagent by maintaining pH in the range of 7.0 to 11.5. Both Gresham and Howk et al. teach that it is essential that the reaction take place in the liquid phase.

U.S. Pat. No. 4,086,262 to Chang et al. describes the production of hydrocarbon mixtures by contacting a mixture of carbon monoxide and hydrogen with a carbon monoxide reduction catalyst and an acidic crystalline alumino silicate (zeolite). Chang et al. teach that prominent types of catalysts include metals or oxides of Zn, Fe, Co, Ni, Ru, Th, Rh, and Os, and that "with the exception of ruthenium, all practical art recognized synthesis catalysts contain chemical and structural promotors."

U.S. Pat. No. 4,171,320 to Vannice discloses the selective production of olefins from carbon monoxide and hydrogen using as a catalyst, ruthenium on a support comprising at least one refractory Group VB metal oxide.

U.S. Pat. No. 4,199,522 to Murchison et al. discloses the preparation of olefins of 2 to 4 carbon atoms from carbon monoxide and hydrogen using catalysts comprising a sulfide, oxide or metal of Mo, W, Re, Ru, Ni, Pd, Rh, Os, Ir or Pt and a hydroxide, oxide or salt of Li, Na, K, Rb, Cs, Mg, Ca, Sr, Ba or Th.

U.S. Pat. No. 4,215,019 to Drake et al. discloses the use of an elemental ruthenium, elemental gold and elemental cobalt combination catalyst in the hydrogenation of unsaturated nitriles.

U.S. Pat. No. 4,206,134 to Kugler et al. discloses the selective preparation of low weight olefins from carbon monoxide and hydrogen using as a catalyst, ruthenium on a support consisting of a manganese-containing oxide.

U.S. Pat. No. 4,246,186 to Bhasin et al. discloses the preparation of two carbon atom oxygenated hydrocarbons from hydrogen and carbon monoxide by reaction with a rhodium metal catalyst, as compared to other single element Group VIII metal and copper catalysts.

SUMMARY OF THE INVENTION

It is an object of the present invention to provide a process to upgrade synthesis gas to produce hydrocarbons, particularly olefins, and oxygenated hydrocarbons, particularly alcohols and carboxylic acids, with high selectivity.

It is a further object of the present invention to provide novel catalyst compositions useful in the upgrading of synthesis gas to produce olefins and oxygenated hydrocarbons, particularly alcohols and carboxylic acids.

We have found that catalysts comprising ruthenium oxide and metallic gold are useful for the upgrading of synthesis gas to hydrocarbons, exhibiting good selectivity to olefins and oxygenated hydrocarbon products, particularly alcohols and carboxylic acids.

In general, the process of the present invention includes the upgrading of synthesis gas to obtain predominantly olefins, alcohols and carboxylic acids, comprising contacting carbon monoxide and hydrogen in the vapor phase at a reaction temperature of at least 250° C. and a reaction pressure of at least 500 psi with a catalyst of the formula $$RuO_x/Au_a\cdot$$

wherein
a is about 0.5 to about 1.5 and
x is the number of oxygens needed to fulfill the valence requirements of the other elements.

The present invention further includes the upgrading of synthesis gas to yield hydrocarbons, alcohols and esters useful for fuels, comprising:
contacting carbon monoxide and hydrogen in the vapor phase at a temperature of at least 250° C. and a pressure of at least 500 psi in the presence of a catalyst of the formula $$RuO_x/Au_a\cdot$$

wherein
a is about 0.5 to about 1.5 and
x is the number of oxygens needed to satisfy the valence requirements of the other elements;
recovering the hydrocarbon and oxygenated hydrocarbon products;
contacting said products with hydrogen at elevated temperature and pressure in the presence of a hydrogenation catalyst.

The present invention further includes novel catalysts of the composition $$RuO_x/Au_a\cdot$$

wherein
a is about 0.5 to about 1.5 and
x is the number of oxygens needed to satisfy the valence requirements of the other elements.

DETAILED DESCRIPTION OF THE INVENTION

In the process of the present invention, synthesis gas, or a mixture of carbon monoxide and hydrogen is reacted in the presence of a carbon monoxide hydrogenation catalyst in the vapor phase to form hydrocarbons, and in particular, olefins, alcohols and carboxylic acids.

Synthesis gas may be produced by means known in the art and practiced commercially, including providing synthesis gas as a product of the partial combustion of coal, natural gas, petroleum bottoms or other carbonaceous materials. One method of derivation is the heating of coke in the presence of air and then steam. The ratio of carbon monoxide to hydrogen in the synthesis gas mixture to be upgraded may vary from about 0.1:1 to 10:1 and is preferably in the range of about 1:3 to about 3:1. The synthesis gas may contain a very low amount of sulfur compounds, and may also contain small amounts of carbon dioxide, nitrogen and other inerts.

Although synthesis gas is a preferred reactant, any other gas mixture composed primarily of hydrogen and carbon monoxide and having a CO:H$_2$ ratio of 0.1:1 to 10:1 may be employed. Preferably the gaseous reactant is essentially sulfur free.

Process Conditions

The process of the present invention is carried out by contacting the gaseous reactants, containing carbon monoxide and hydrogen, with the novel catalyst described below in a suitable fluid bed or fixed bed reactor. The reaction can be conducted continuously or in a batch-type operation. The reaction temperature should be maintained between about 250° C. to about 400° C., preferably between about 300° C. to about 375° C.

The reaction pressure should normally be maintained between about 500 psi to about 5,000 psi, preferably between about 500 psi to about 1500 psi. The reactant gases may be fed to the reactor utilized at a space velocity (liters gaseous reactants fed per liters of catalyst per hour) of about 100 per hour to about 10,000, preferably about 500 per hour to 5,000 per hour.

The contact time of the reactants with the catalyst is generally between about 10 seconds to about 200 seconds, and is preferably about 40 seconds to about 140 seconds.

Catalyst

The novel catalyst provided by the present invention is believed to be a mixture or a complex of ruthenium oxide and elemental gold and comprises the composition described by the empirical formula $$RuO_x/Au_a°$$

wherein
a is about 0.5 to about 1.5 and
x is the number of oxygens needed to fulfill the valence requirements of the other elements.

The molar ratio of ruthenium to gold is critical, with higher Ru/Au ratios resulting in paraffin wax production, and lower Ru/Au ratios resulting in either methane or paraffin wax production. Catalysts consisting substantially of metallic or elemental gold exhibit little or no activity. The preferred Ru/Au ratio is 1:1.

The catalyst of the present invention contains ruthenium oxide. In the process of the present invention, the catalyst is preferably utilized in a partially reduced state. The ruthenium of the catalyst, however, is thought not to be totally reduced to elemental metal and thus retains its oxide character.

The catalyst may be prepared by conventional means, such as mixing compounds containing the catalyst components in a liquid solution or slurry, such as a water solution or slurry and heating; recovering the catalyst precursor from the liquid, drying and calcining. Catalyst containing compounds may include but are not limited to oxides, hydroxides, inorganic salts such as nitrates, phosphates, halides, carbonates, silicates, aluminates, and salts of organic acids such as acetates, formates, butyrates, propionates, benzylates, and the like.

The catalyst may be formed in a conventional manner, such as tabletting, pelleting, or supporting the active catalyst material on a carrier. The carrier is preferably inert, and may include silica, alumina, Alundum, clay, alumina-silica, silicon carbide and the like. The active catalytic material may be coated on the carrier by the method described in U.S. Pat. No. 4,077,912 or may be impregnated on the carrier such as by depositing a solution of the catalyst component containing compounds onto a carrier, drying and calcining.

Products

Products of the synthesis gas upgrading process of the present invention include methane, gaseous alkanes and olefins having more than one carbon atom up to about 4 carbon atoms; alcohols, acids and aldehydes having from one to five carbon atoms present in an aqueous product phase; and olefins, alcohols, acids, esters and aldehydes having from four carbon atoms up to about 18 carbon atoms in an organic or oil product phase.

Products include, among others, methane, ethane, propane, butane, ethylene, propylene, butene, methanol, ethanol, propanol, butanol, acetic acid, propanoic acid, butanoic acid, acetaldehyde, propionaldehyde and butyraldehyde.

The products of the present invention are useful as fuels, such as in gasoline mixtures, or as chemical feedstocks. Alkanes, esters and alcohols are most suitable for use as fuels, such as in gasoline mixtures. Thus, in one embodiment of the invention, the liquid product mixture obtained from the synthesis gas upgrading process (containing in addition to alcohols, the non-fuel components such as olefins, aldehydes and carboxylic acids) is contacted with hydrogen at elevated temperature and pressure in the presence of a hydrogenation catalyst. The resulting hydrogenation products, alkanes, alcohols and esters, are suitable for use as fuel components.

The hydrogenation process may be conducted in the vapor phase, at a reaction temperature of about 150° C. to about 450° C. and a reaction pressure of about 250 psig to about 5000 psig. Any suitable hydrogenation catalyst such as nickel or copper chromite may be used, although catalysts such as those disclosed in U.S. Ser. No. 264,755, assigned to our common assignee, are preferred. These catalysts may be represented by the formula:

$$G_eRu_fD_gE_hO_x$$

wherein
G = Zn, Cd and mixtures thereof;
D = Co, Ni and mixtures thereof;
E = Fe, Cu, Rh, Pd, Os, Ir, Pt and mixtures thereof;
and wherein
e = 0 to 1,
f = 0.01 to 3,
g = 0.01 to 3,
h = 0 to 1,
x = the number of oxygens determined by the valence requirements of the other elements.

SPECIFIC EMBODIMENTS

Catalyst Preparation

Gold oxide was heated to decomposition to elemental gold at 250° C., and was mixed with ruthenium oxide in amounts calculated to give the Ru/Au ratios listed in the examples below.

The catalyst components were coated upon alumina-silica supports in the following manner. 25 grams of Norton SA 5223 Alundum, 10/30 mesh (0.595 millimeters-2.00 millimeters) were placed in a vessel. 1.25 grams distilled water was sprayed onto the Alundum which was rolled for approximately 10 minutes and the procedure was repeated. For catalysts having a Ru/Au ratio of 1, the metallic gold and ruthenium metal oxide catalyst components, in an amount calculated to give a total of 0.015 moles of active metal, were added in two equal portions with 15 minutes rolling after each. The coated catalyst was dried for about 16 hours at 125° C. and calcined three hours at 350° C. Catalysts prepared in this manner contain approximately 5 weight percent active metals, and have surface areas of about 2 square meters per gram, with pore volumes of from about 0.06 to about 0.09 cc/g.

The ruthenium oxide component of the catalysts was partially reduced in the following manner. A 20 cc stainless steel tube reactor was packed with catalyst, and hydrogen gas was introduced into the reactor at 150–200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued.

Reaction Procedure

Following catalyst reduction and subsequent cooling to room temperature, the reactor utilized was charged to the desired pressure with hydrogen. The split block electric furnace surrounding the reactor was activated and set for run temperature. The system was allowed to equilibrate for at least 15 minutes at run temperature before carbon monoxide flow was started and both gases were adjusted to the desired flow rates. After about one to one and one-half hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid product also was weighed and analyzed.

In addition to gas chromatography analysis for the gas phase, hydrocarbons having greater than three carbon atoms were determined by flame ionization detection. Liquid phase hydrocarbons and oxygenated hydrocarbons were analyzed by gas chromatography. The results reported in the Tables below were calculated as follows.

Selectivity =

$$\frac{\text{Moles Product} \times \text{number carbon atoms in product}}{\text{Moles CO input} - \text{Moles CO effluent}} \times 100$$

CO Conversion =

$$\frac{\text{Moles of CO input} - \text{moles CO effluent}}{\text{Moles of CO input}} \times 100$$

Selectivity to gas and aqueous phase products are reported as a percent of total products. Selectivity to oil phase products are reported as a mole percent of total oil phase product obtained, calculated as above. Weight % higher alkanes are reported as a percent of oil phase product. Carbon dioxide and water are not considered in the calculations.

EXAMPLES 1–8

Catalysts of the formula 5% $RuO_x/Au^*$—95% Alundum were prepared according to the procedure set forth above. The catalysts were tested for synthesis gas upgrading under reaction conditions listed in Table I below. Test results are reported in Tables I and II below. Products included oxygenated hydrocarbons and olefins in three phases, including gas, aqueous and organic or oil phase.

Comparative Examples A&B

Catalysts of the formula 5% $RuO_x/Au_2$—95% Alundum were prepared according to the procedure of examples 1–8, except that a Ru/Au* molar ratio of 1:2 was effected by altering amounts of catalyst components utilized. The catalysts were tested for synthesis gas upgrading under reaction conditions listed in Table IIIA below. Test results are reported in Tables IIIA and IIIB below. At low $CO:H_2$ ratios, these catalysts had low CO conversion resulting mainly in methane production. At higher $CO:H_2$ ratios, low CO conversion resulted in a product mix, but with low selectivity to lower oxygenated hydrocarbons, and no selectivity to either higher olefins or oxygenated hydrocarbons.

EXAMPLE 9

A catalyst of the formula 5% $RuO_x/Au_{0.5}^*$—95% Alundum was prepared according to the procedure of examples 1–8, except that a Ru/Au* ratio of 2:1 was effected by altering amounts of catalyst components utilized. The catalysts were tested for synthesis gas upgrading under reaction conditions listed in Table IIIA below. Test results are reported in Tables IIIA and IIIB below. Major products were oxygenated hydrocarbons including alcohols and carboxylic acids, and olefins.

EXAMPLES 10–12

Catalysts of the formula 5% $RuO_x/Au^*$—95% Alundum were prepared according to the procedure of examples 1–8. The catalysts were tested for synthesis gas upgrading under reaction conditions listed in Table IIIA below. Test results are reported in Tables IIIA and IIIB below. Major products were oxygenated hydrocarbons including alcohols and carboxylic acids, and olefins.

The products of the synthesis gas upgrading process of the present invention generally exhibit increased carbon chain length upon increase in reaction temperature and/or pressure. In addition, increased reaction temperature causes an increased selectivity to alcohols and decreased selectivity to olefins, particularly in the organic phase (larger carbon chain length) products. High space velocity generally favors production of unsaturates and smaller chain length products.

In one embodiment of the invention, $C_1$–$C_3$ products predominate when reaction temperature is maintained in a range between about 320° C. to about 350° C., pressure is maintained between about 600 psi to about 1000 psi, and the space velocity is about 4500/hr. In another embodiment of the invention, products having more than about four carbon atoms predominate when reaction temperature is about 360° C., pressure is about 1300 psi, and space velocity is maintained between about 2000–3300/hr.

As an example of the product mix produced by the inventive process, the products obtained by testing the catalyst of Example 3 are as follows.

| Product | Weight (grams) |
| --- | --- |
| Methane | 1.1456 |
| Ethane | 0.2795 |
| Propane | 0.2426 |
| Ethylene | 0.3808 |
| Propylene | 0.4998 |
| Methanol | 0.1061 |
| Ethanol | 0.1395 |
| Propanol | 0.0502 |
| Butanol | 0.0258 |
| Pentanol | 0.0056 |
| Acetic Acid | 0.1928 |
| Propionic Acid | 0.0987 |
| Butyric Acid | 0.0408 |
| Valeric Acid | 0.0187 |
| Aldehydes | 0.1118 | hydrogenated products of the process of the present invention, alkanes, alcohols and esters, are useful for fuels.

Thus it should be apparent to those skilled in the art that the subject invention accomplishes the objects set forth above. It is to be understood that the subject invention is not to be limited by the examples set forth herein. These have been provided merely to demonstrate operability and the selection of catalyst component containing compounds, catalyst formulations, synthesis gas component ratios and reaction conditions can be determined from the total specification disclosure provided without departing from the spirit of the invention herein disclosed and described. The scope of the invention includes equivalent embodiments, modifications and variations that fall within the scope of the attached claims.

TABLE I

UPGRADING OF SYNTHESIS GAS USING 5% $RuO_x$-$Au^o$/95% ALUNDUM CATALYSTS

| Example No. | Temp. (°C.) | Pressure (PSI) | CO:$H_2$ Ratio | Space Velocity | % CO Conversion | Wt. % Hydrocarbon Prod. | | | % Selectivity | |
| --- | --- | --- | --- | --- | --- | --- | --- | --- | --- | --- |
| | | | | | | Gaseous | Aqueous | Oil | Hydrocarbons(g) | Oxygenates |
| 1 | 350 | 1300 | 3:7 | 3300 | 44.1 | 45.2 | 9.7 | 45.2 | 31.9 | 3.5 |
| 2 | 320 | 1300 | 3:7 | " | 6.1 | 77.1 | 22.9 | — | 58.0 | 11.3 |
| 3 | 360 | 1300 | 3:7 | " | 48.7 | 40.5 | 10.6 | 49.0 | 28.6 | 4.5 |
| 4 | 360 | 1000 | 3:7 | " | 31.3 | 48.0 | 11.2 | 40.8 | 28.8 | 4.0 |
| 5 | 360 | 600 | 3:7 | " | 9.3 | 83.2 | 16.8 | — | 38.1 | 4.4 |
| 6 | 360 | 1300 | 3:7 | 2000 | 99.1 | 41.2 | 8.7 | 50.2 | 21.6 | 2.7 |
| 7 | 360 | 1300 | 3:7 | 4500 | 33.4 | 34.5 | 8.9 | 56.6 | 32.7 | 4.9 |
| 8 | 360 | 1300 | 5:7 | 4500 | 22.4 | 37.1 | 9.9 | 53.0 | 22.1 | 3.4 | g = gaseous

TABLE II

UPGRADING OF SYNTHESIS GAS USING 5% $RuO_x$/95% ALUNDUM CATALYSTS

| Example No. | % Selectivity (Gas Phase) | | | % Selectivity (Aqueous)* | | % Selectivity (Oil) | | | | Wt. % Higher Alkanes |
| --- | --- | --- | --- | --- | --- | --- | --- | --- | --- | --- |
| | $CH_4$ | Alkanes | Olefins | Alcohols | Acids | Alcohols | Acids | Aldehydes | Olefins | |
| 1 | 13.3 | 7.0 | 11.6 | 1.7 | 1.8 | 13.3 | 39.8 | 2.1 | 44.8 | — |
| 2 | 22.9 | 6.7 | 28.4 | 0.5 | 10.8 | — | — | — | — | — |
| 3 | 12.1 | 5.9 | 10.6 | 2.3 | 2.2 | 29.0 | 37.3 | 4.4 | 29.3 | 15 |
| 4 | 11.6 | 5.4 | 11.8 | 1.7 | 2.3 | 25.7 | 44.1 | 5.0 | 25.2 | 9 |
| 5 | 17.2 | 2.8 | 18.1 | 0.9 | 3.5 | — | — | — | — | — |
| 6 | 11.9 | 6.9 | 2.8 | 1.5 | 1.3 | 23.9 | 30.6 | 1.6 | 44.0 | 34 |
| 7 | 12.8 | 6.7 | 13.2 | 2.1 | 2.8 | 19.3 | 31.3 | 5.8 | 43.6 | 16 |
| 8 | 7.3 | 4.4 | 10.4 | 1.4 | 2.1 | 22.5 | 33.9 | 7.8 | 35.8 | 21 |

*Trace Aldehydes Present

EXAMPLE 13

A portion of the liquid products of the process of the present invention, comprising mainly carboxylic acids and olefins, with minor amounts of alcohols and aldehydes, were hydrogenated in the vapor phase at a reaction temperature of 200° C. and a pressure of 1000 psi in the presence of a hydrogenation catalyst comprising 5% $RuCoPdZn_{0.4}O_x$ on 95% Alundum. Hydrogen was introduced to the reaction at 300 cc/minute, and hydrocarbon liquid was introduced to the reaction at 5 cc/hour. Olefins and aldehydes were completely converted to alkanes and alcohols, and over 90% of the acids were converted to either alcohols or esters. The

TABLE IIIA

UPGRADING OF SYNTHESIS GAS

| Example No. | Catalyst (Active)* | Temperature °C. | Pressure (PSI) | CO:$H_2$ Ratio | Space Velocity | % CO Conversion |
| --- | --- | --- | --- | --- | --- | --- |
| Comp. A | $RuO_x$/$Au_2^o$ | 350 | 1300 | 3:7 | 3300 | — |
| Comp. B | $RuO_x$/$Au^{2o}$ | 350 | 1300 | 8:7 | 3300 | 15.1 |
| 9 | $RuO_x$/$Au^{0.5o}$ | 350 | 1300 | 1:1 | 1650 | 49.4 |
| 10 | $RuO_x$/$Au^o$ | 320 | 1300 | 3:7 | 3300 | 29.9 |
| 11 | $RuO_x$/$Au^o$ | 320 | 1300 | 3:7 | 3300 | 31.8 |
| 12 | $RuO_x$/$Au^o$ | 320 | 1300 | 3:7 | 3300 | 19.4 |

*5% on Alundum

TABLE IIIB

UPGRADING OF SYNTHESIS GAS

| Example No. | % Selectivity (Gas) | | | % Selectivity (Aqueous$^a$) | | % Selectivity (Oil) | | | | Wt. % Higher Alkanes |
| --- | --- | --- | --- | --- | --- | --- | --- | --- | --- | --- |
| | $CH_4$ | Alkanes | Olefins | Aqueous | Acids | Alcohols | Acids | Aldehydes | Olefins | |
| Comp. A | 100 | — | — | — | — | — | — | — | — | — |
| Comp. B | — | 10.2 | 13.2 | 1.5 | 0.7 | — | — | — | — | b |
| 9 | — | 2.4 | 5.7 | 0.7 | 0.5 | 15.5 | 21.4 | 3.3 | 59.9 | 39 |
| 10 | c | 4.8 | 9.4 | 1.3 | 0.8 | 21.0 | 19.4 | 4.6 | 55.1 | 27 |
| 11 | c | 5.7 | 7.5 | 1.4 | 0.3 | 21.8 | 12.1 | 3.5 | 62.7 | 34 |

TABLE IIIB-continued
UPGRADING OF SYNTHESIS GAS

| Example No. | % Selectivity (Gas) | | | % Selectivity (Aqueous[a]) | | % Selectivity (Oil) | | | | Wt. % Higher Alkanes |
|---|---|---|---|---|---|---|---|---|---|---|
| | CH$_4$ | Alkanes | Olefins | Aqueous | Acids | Alcohols | Acids | Aldehydes | Olefins | |
| 12 | c | 7.6 | 10.2 | 2.6 | 1.2 | 30.7 | 8.9 | 3.4 | 57.1 | c |

[a]Trace Aldehydes Present
[b]Paraffin Wax
[c]Not Determined

We claim:

1. A process for the upgrading of synthesis gas with good selectivity to olefins and oxygenated hydrocarbons comprising contacting carbon monoxide and hydrogen in the vapor phase at a temperature of at least 250° C. and a pressure of at least 500 psi in the presence of a catalyst of the formula $$RuO_x/Au_a\cdot$$

wherein
a = about 0.5 to about 1.5 and
x = number of oxygens needed to satisfy the valence requirements of the other elements.

2. A process as in claim 1 wherein the CO:H$_2$ ratio is between about 10:1 to 1:10.

3. A process as in claim 1 wherein the CO:H$_2$ ratio is between about 3:1 to about 1:3.

4. A process as in claim 1 wherein the pressure is between about 500 psi to about 5000 psi.

5. A process as in claim 1 wherein the temperature is between about 250° C. and 400° C.

6. A process as in claim 1 wherein the ruthenium component of the catalyst is at least partially reduced.

7. A process as in claim 1 or 6 wherein a is about 1.

8. A process as in claim 1, 6 or 7 wherein said catalyst is supported on a carrier.

9. A process as in claim 8 wherein said carrier is essentially inert and is selected from alumina, silica, clay, alumina-silica, Alundum, and silicon carbide.

10. A process as in claim 1 wherein the temperature is about 320° C. to about 350° C., and the pressure is about 600 psi to about 1000 psi.

11. A process as in claim 1 wherein the temperature is about 360° C. and the pressure is about 1300 psi.

12. A process for the upgrading of synthesis gas to yield hydrocarbons, alcohols and esters useful for fuel, comprising
contacting carbon monoxide and hydrogen in the vapor phase at a temperature of at least 250° C. and a pressure of at least 500 psi in the presence of a catalyst of the formula $$RuO_x/Au_a\cdot$$

wherein
a = about 0.5 to about 1.5 and
x = number of oxygens needed to satisfy the valence requirements of the other elements;
recovering the resulting hydrocarbon and oxygenated hydrocarbon products; and
contacting said products with hydrogen at elevated temperature and pressure in the presence of a hydrogenation catalyst.

13. A process as in claim 12 wherein said products are contacted with hydrogen at a temperature of at least 200° C.

14. A process as in claim 12 wherein said products are contacted with hydrogen at a pressure of about 500 psi to 5000 psi.

15. A process as in claim 12 wherein said hydrogenation catalyst is represented by the formula $$G_eRu_fD_gE_hO_x$$

wherein
A = Zn, Cd and mixtures thereof;
D = Co, Ni and mixtures thereof;
E = Fe, Cu, Rh, Pd, Os, Ir, Pt and mixtures thereof;
and wherein
e = 0 to 1,
f = 0.01 to 3,
g = 0.01 to 3,
h = 0 to 1,
x = the number of oxygens determined by the valence requirements of the other elements.

16. A process as in claim 15 wherein said hydrogenation catalyst has the formula $RuCoPdZn_{0.4}O_x$.

* * * * *